United States Patent
Okugawa (10) Patent No.: US 7,639,357 B2
(45) Date of Patent: Dec. 29, 2009

(54) LASER SCANNING MICROSCOPE

(75) Inventor: Hisashi Okugawa, Yokosuka (JP)

(73) Assignee: Nikon Corporation, Tokyo (JP)

(*) Notice: Subject to any disclaimer, the term of this patent is extended or adjusted under 35 U.S.C. 154(b) by 0 days.

(21) Appl. No.: 12/318,014

(22) Filed: Dec. 19, 2008

(65) Prior Publication Data

US 2009/0147256 A1    Jun. 11, 2009

Related U.S. Application Data

(63) Continuation of application No. PCT/JP2007/000657, filed on Jun. 20, 2007.

(30) Foreign Application Priority Data

Jul. 3, 2006    (JP) ............... 2006-183579

(51) Int. Cl.
*G01N 21/64* (2006.01)
*G01J 3/30* (2006.01)
(52) U.S. Cl. .................... 356/318; 359/372
(58) Field of Classification Search ........... 356/318; 359/372, 373
See application file for complete search history.

(56) References Cited

U.S. PATENT DOCUMENTS 6,094,300 A    7/2000    Kashima et al.

FOREIGN PATENT DOCUMENTS

| JP | A-10-206742 | 8/1998 |
|----|---|---|
| JP | 2000-97857 | * 4/2000 |
| JP | A-2005-189290 | 7/2005 |
| JP | A-2006-3521 | 1/2006 |
| JP | A-2006-119347 | 5/2006 |

* cited by examiner

Primary Examiner—F. L Evans
(74) Attorney, Agent, or Firm—Oliff & Berridge, PLC (57) ABSTRACT

To provide a laser scanning microscope capable of enhancing the degree of freedom of observation while keeping its structure simple. Accordingly, a laser scanning microscope includes a light source, a spectroscopic unit guiding light from the light source to a specimen and guiding the light from the specimen to a detector, light path switching units switching a light path between the spectroscopic unit and the specimen to one among a plurality of light paths with different routes, and a plurality of light deflecting units each disposed in each of the plurality of light paths.

9 Claims, 8 Drawing Sheets

LASER SCANNING MICROSCOPE

CROSS-REFERENCE TO RELATED APPLICATION

This application is a Continuation Application of International Application No. PCT/JP2007/000657, filed Jun. 20, 2007, designating the U.S., in which the International Application claims a priority date of Jul. 3, 2006, based on prior filed Japanese Patent Application No. 2006-183579, the entire contents of which are incorporated herein by reference.

BACKGROUND

1. Field

The present invention relates to a laser scanning microscope such as a confocal laser scanning microscope and a confocal fluorescence laser scanning microscope.

2. Description of the Related Art

There has been proposed a laser scanning microscope in which an optical system for light stimulus is combined with an optical system for imaging (refer to Patent Document 1: Japanese Unexamined Patent Application Publication No. H10-206742). With the use of this microscope, it is possible to apply a stimulus to a part of a sample with light of specific wavelength and to observe a change generated in the periphery of the part of the sample (light stimulus observation).

The laser scanning microscope includes a plurality of scanning optical systems and one detecting optical system, in which the detecting optical system is optically coupled to a sample via one scanning optical unit among the plurality of scanning optical systems (refer to Patent Document 2: Japanese Unexamined Patent Application Publication No. 2005-189290). Therefore, a fluorescence generated from a fluorescent reagent exited by a first light beam advances in the opposite direction along the same light path as that of the first light beam and guided to the detecting optical system. Further, a fluorescence generated from a fluorescent reagent exited by a second light beam also advances in the opposite direction along the same light path as that of the first light beam and guided to the detecting optical system.

However, in the microscope disclosed in Patent Document 1, the optical system for light stimulus exists independently from the optical system for imaging, so that both a light source and a galvanometer scanner disposed in the optical system for light stimulus can be used only for applying the light stimulus.

For instance, even if an imaging wavelength and a light stimulus wavelength of a certain sample are the same, there is a need to mount each one of the same light sources on both the optical system for imaging and the optical system for light stimulus.

Further, in the microscope disclosed in Patent Document 2, the fluorescence generated from the fluorescent reagent exited by the second light beam is guided to the detecting optical system by using a first scanning unit (scanner) which is different from a second optical scanning unit (scanner) used for scanning with the second light beam, so that the both scanners have to be the same type, and to obtain images, they have to be synchronized in an accurate manner.

SUMMARY

Accordingly, a proposition of the present invention is to provide a laser scanning microscope capable of enhancing the degree of freedom of observation while keeping its structure simple.

A laser scanning microscope of the present invention includes a light source, a optical unit guiding light from the light source to a specimen and guiding the light from the specimen to a detector, light path switching units switching a light path between the optical unit and the specimen to one among a plurality of light paths with different routes, and a plurality of light deflecting units each disposed in each of the plurality of light paths.

Note that the light path switching units may include mirrors capable of being inserted into and/or removed from respective branching points of the plurality of light paths.

Further, a laser scanning microscope of the present invention includes a light source, a optical unit guiding light from the light source to a specimen and guiding the light from the specimen to a detector, light path setting units separating a light path between the optical unit and the specimen into a plurality of light paths with different routes, and a plurality of light deflecting units each disposed in each of the plurality of light paths.

Note that the light path setting units may include beam splitters disposed in respective branching points of the plurality of light paths.

Further, the light source may be provided with a plurality of kinds of light sources with different wavelengths.

Further, either one of the plurality of light deflecting units may include a resonant galvanometer scanner.

According to the present invention, a laser scanning microscope capable of enhancing the degree of freedom of observation while keeping its structure simple is realized.

DETAILED DESCRIPTION OF THE EMBODIMENTS

First Embodiment

Hereinafter, a first embodiment will be explained. The present embodiment is an embodiment of a confocal fluorescence laser scanning microscope system.

First, a structure of the present system will be described.

Figure 1:
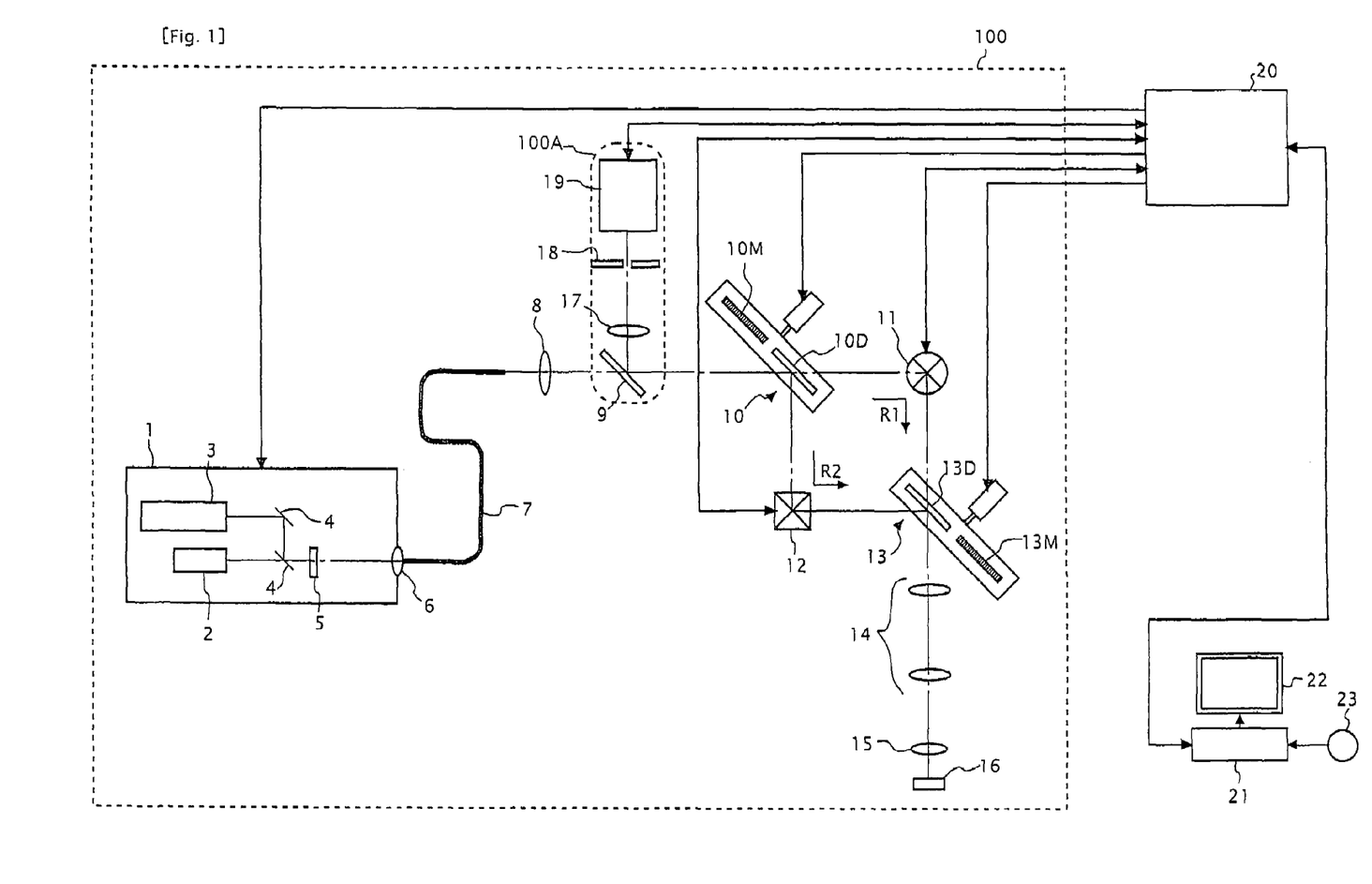
FIG. 1 is a structural view of a system of a first embodiment.

FIG. 1 is a structural view of the present system. As shown in FIG. 1, the present system includes a main body of microscope 100, a controller 20, a computer 21, a monitor 22, an input device 23 and the like.

In the main body of microscope 100, a laser unit 1, an optical fiber 7, a collimating lens 8, a dichroic mirror 9, a light path switching unit 10, a controllable galvanometer scanner 11, a light path switching unit 13, a resonant galvanometer scanner 12, a relay lens 14, an objective lens 15, a sample 16, a collecting lens 17, a pinhole diaphragm for confocal detection 18, a light detector 19 and the like are disposed. Among them, the dichroic mirror 9, the collecting lens 17, the pinhole diaphragm 18 and the light detector 19 form a detecting optical system 100A. Note that the sample 16 is a sample for observing fluorescence (sample to which a fluorescent dye is added) supported on a not-shown stage.

The controllable galvanometer scanner 11 is provided with a galvanometer mirror for main scanning and a galvanometer mirror for vertical scanning which are disposed in serial relationship, and the resonant galvanometer scanner 12 is provided with a resonant galvanometer mirror for main scanning and a controllable galvanometer mirror for vertical scanning which are disposed in serial relationship. Between the two scanners, the controllable galvanometer scanner 11 has an advantage that a scanning area can be freely set although a scanning speed is slow, which is effective when an irradiation target of laser light is limited to a desired partial area of an observation area of the sample 16, and the resonant galvanometer scanner 12 has an advantage that a scanning speed is fast although it is difficult to freely set a scanning area, which is effective when performing laser scanning over the sample 16 at high speed.

A plurality of kinds of laser light sources (here, two laser light sources 2 and 3) are mounted on the laser unit 1. Emission light paths of the laser light sources 2 and 3 are combined into a common light path by a combining mirror 4, and in the common light path, an acoustic optical filter (AOTF) 5 is inserted. By controlling the AOTF 5 and each of the laser light sources 2 and 3, the laser unit 1 performs a setting of the applied light sources, an on/off control of the emission light, a control of intensity of the emission light, and the like.

Laser light emitted from the laser unit 1 is incident on one end of the optical fiber 7 via a fiber coupler 6. The laser light propagates inside the optical fiber 7, and then it is incident from the other end of the optical fiber 7, and after being turned into parallel pencil of light by the collimating lens 8, it is incident on the dichroic mirror 9. The laser light passes through the dichroic mirror 9 and is incident on a dichroic mirror 10D of the light path switching unit 10.

The laser light with short wavelength transmitted through the dichroic mirror 10D passes through a light path R1, and after being reflected by the controllable galvanometer scanner 11, it is incident on a dichroic mirror 13D of the light path switching unit 13. Since a characteristic of the dichroic mirror 13D is set in the same manner as a characteristic of the dichroic mirror 10D, the laser light passed through the light path R1 transmits through the dichroic mirror 13D, passes through the relay lens 14 and the objective lens 15, and forms a spot on the sample 16. A fluorescence generated from the spot (a wavelength thereof is little longer than that of the laser light) advances in the opposite direction along the same light path R1 as that of the laser light which forms the spot, toward the dichroic mirror 9. When the controllable galvanometer scanner 11 is driven under this state, the spot two-dimensionally scans over the sample 16.

Meanwhile, the laser light with comparatively long wavelength reflected by the dichroic mirror 10D passes through a light path R2 which is different from the light path R1, and after being reflected by the resonant galvanometer scanner 12, it is incident on the dichroic mirror 13D of the light path switching unit 13. Since the characteristic of the dichroic mirror 13D is set in the same manner as that of the dichroic mirror 10D, the laser light passed through the light path R2 is reflected by the dichroic mirror 13D, passes through the relay lens 14 and the objective lens 15, and forms a spot on the sample 16. A fluorescence generated from the spot (a wavelength thereof is little longer than that of the laser light which forms the spot) advances in the opposite direction along the same light path R2 as that of the laser light which forms the spot, toward the dichroic mirror 9. When the resonant galvanometer scanner 12 is driven under this state, the spot two-dimensionally scans over the sample 16.

The fluorescence incident on the dichroic mirror 9 is reflected by the dichroic mirror 9 and taken into the detecting optical system 100A. The fluorescence condensed by the collecting lens 17 and passed through the pinhole diaphragm 18 is incident on the light detector 19 and converted into an electrical signal.

Here, each of the light path switching units 10 and 13 is formed of a turret. The light path switching unit 10 is equipped with the dichroic mirror 10D, an all-reflective mirror 10M and a not-shown hollow block, and can switch an optical element (set element) to be inserted into the light path to one among these three. In like manner, the light path switching unit 13 is equipped with the dichroic mirror 13D, an all-reflective mirror 13M and a not-shown hollow block, and can switch an optical element (set element) to be inserted into the light path to one among these three.

When a combination of set elements of the light path switching units 10 and 13 is set to that of dichroic mirrors 10D and 13D as shown in FIG. 1, a light path between the dichroic mirror 9 and the relay lens 14 is separated into the light path R1 and the light path R2 depending on each wavelength.

Meanwhile, when the combination of set elements of the light path switching units 10 and 13 is set to that of all-reflective mirrors 10M and 13M, the light path between the dichroic mirror 9 and the relay lens 14 takes only the light path R2 without depending on the wavelength.

Further, when the combination of set elements of the light path switching units 10 and 13 is set to that of each of the hollow blocks, the light path between the dichroic mirror 9 and the relay lens 14 takes only the light path R1 without depending on the wavelength.

Now, each of the light path switching units 10 and 13 is electrically-driven by a motor. Note that since it is allowable that the combinations of set elements are only three combinations, which are, the combination of dichroic mirrors 10D and 13D, the combination of all-reflective mirrors 10M and 13M and the combination of respective hollow blocks, a connection destination of the light path switching units 10 and 13 can be a common motor.

Further, the light path switching units 10 and 13 and the other driving parts of the main body of microscope 100 (the laser unit 1, the controllable galvanometer scanner 11, the resonant galvanometer scanner 12, the light detector 19 and the like) are controlled by the controller 20. The controller 20 is under the control of the computer 21, and an instruction from a user is given to the computer 21 via the monitor 22 and the input device 23, and is given to the controller 20 via the computer 21.

In accordance with the instruction from the computer 21, the controller 20 gives necessary instructions and driving signals to the respective driving parts of the main body of microscope 100, to thereby set and drive the main body of microscope 100.

For instance, if the controller 20 takes the electrical signal from the light detector 19 while synchronously driving the laser unit 1, the resonant galvanometer scanner 12 and the light detector 19 after setting the main body of microscope 100 so that the light path R2 is effective, it is possible to obtain (to perform an imaging of) fluorescence image data of an observation area of the sample 16. The fluorescence image data is transmitted from the controller 20 to the computer 21, and then transmitted to the monitor 22 or stored in the computer 21 if necessary.

As described above, the main body of microscope 100 of the present system disposes, with the use of the light path switching units 10 and 13, a pair of galvanometer scanners (the controllable galvanometer scanner 11 and the resonant galvanometer scanner 12) in parallel relationship with respect to the light paths between the dichroic mirror 9 and the sample 16, so that one laser unit 1 and one detecting optical system 100A are used in common by the pair of galvanometer scanners (the controllable galvanometer scanner 11 and the resonant galvanometer scanner 12).

Therefore, the main body of microscope 100 of the present system can select a destination of an incident light of the laser unit 1 between the pair of galvanometer scanners and to select a galvanometer scanner used for the imaging between the pair of galvanometer scanners, although it is equipped with only one laser unit 1 and only one detecting optical system 100A.

Further, since the light path switching units 10 and 13 are provided with beam splitters (here, the dichroic mirrors 10D and 13D) as one of the optical elements capable of being inserted into the light paths, they are also get the laser light from the laser unit possible to simultaneously incident onto the pair of galvanometer scanners (the controllable galvanometer scanner 11 and the resonant galvanometer scanner 12).

Note that in the main body of microscope 100 of the present system, the branching points of the light paths R1 and R2 on which the pair of galvanometer scanners is disposed are between the dichroic mirror 9 and the relay lens 14, but, they may be between the relay lens 14 and the objective lens 15 or in a light path of the relay lens 14. However, if either of the branching points is set in the light path of the relay lens 14, there is a need to dispose a part of the relay lens on each of the light paths R1 and R2, resulting that the number of optical elements is increased a little.

Further, in the main body of microscope 100 of the present system, the light path switching units 10 and 13 are formed of the turrets, but, they may be formed of other mechanisms such as slide mechanisms.

Further, in the main body of microscope 100 of the present system, the light path switching units 10 and 13 are electrically-driven by the motors, but, the motors may be omitted and the switching operation may be conducted manually.

Second Embodiment

Hereinafter, a second embodiment will be described. The present embodiment is an embodiment of a light stimulus observation method in which a light stimulus and an imaging are simultaneously performed using the system of the first embodiment.

Here, an excitation wavelength of the fluorescent dye applied to the sample 16 is set to 488 nm, and a wavelength of the light stimulus to be given to the sample 16 is set to 405 nm.

In this case, the respective parts of the main body of microscope 100 are set as follows, for instance.

Laser light source 2: ultraviolet laser light source (wavelength of 405 nm)

Laser light source 3: argon laser light source (wavelength of 488 nm)

Figure 2:
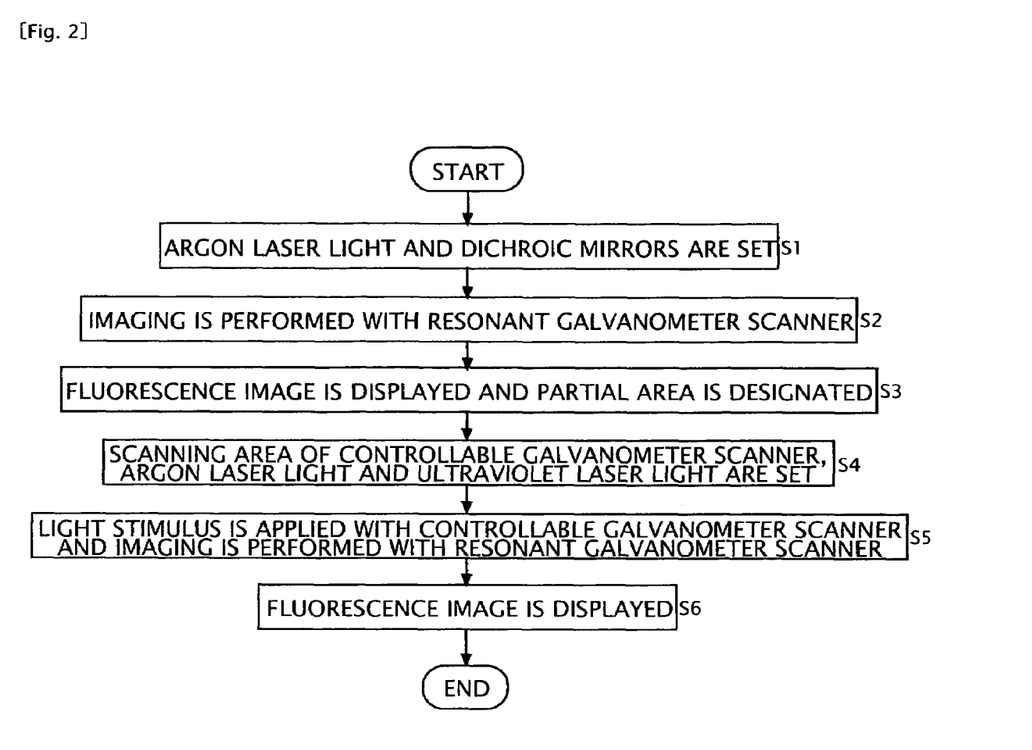
FIG. 2 is a view showing a procedure in a second embodiment.

Dichroic mirror 9: dichroic mirror which transmits light of a short wavelength side including 488 nm and reflects light of a long wavelength side longer than 488 nm Dichroic mirrors 10D and 13D: dichroic mirrors which transmit light of a short wavelength side shorter than 488 nm and reflects light of a long wavelength side including 488 nm A procedure of the light stimulus observation is as shown in FIG. 2.

(Step 1)

Figure 3:
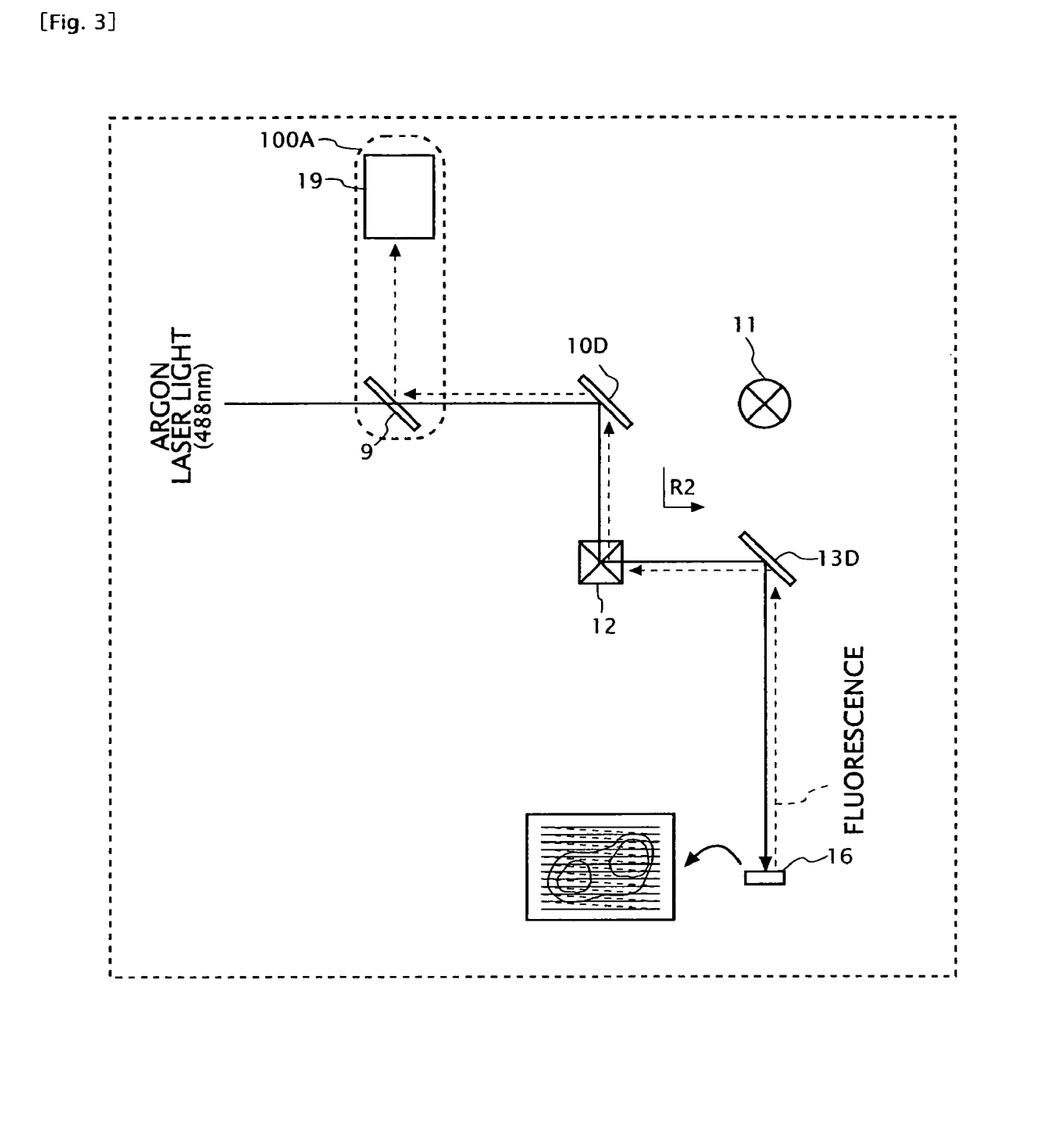
FIG. 3 is a conceptual diagram to explain a light path of argon laser light in the second embodiment.

The controller 20 sets the applied light source of the laser unit 1 to the laser light source 3 (argon laser light source), and sets the combination of set elements of the light path switching units 10 and 13 to that of dichroic mirrors 10D and 13D as shown in FIG. 3.

At this time, the laser light capable of being emitted from the laser unit 1 is only the argon laser light with 488 nm of wavelength. This argon laser light can reach the sample 16 by passing through the light path R2 as shown by a solid line in FIG. 3, and a spot of the argon laser light can scan over an entire observation area of the sample 16 (refer to a lower part in FIG. 3) using the resonant galvanometer scanner 12. Since a fluorescence generated from the spot can be reflected by the dichroic mirror 9 as shown by a dotted line in FIG. 3, it is extracted to a side of the detecting optical system 100A.

(Step 2)

The controller 20 drives the laser unit 1, the resonant galvanometer scanner 12 and the light detector 19, and performs an imaging of the entire observation area of the sample 16 (refer to the lower part in FIG. 3) with the argon laser light. Fluorescence image data of the sample 16 obtained through this imaging is transmitted to the computer 21.

(Step 3)

The computer 21 outputs the fluorescence image data of the sample 16 to the monitor 22 and gets a user to designate, on a screen of the monitor 22, a partial area to which the light stimulus is applied. Through the operation of the input device 23, the user designates a desired partial area with respect to the computer 21. Information regarding the partial area designated by the user is transmitted to the controller 20.

(Step 4)

The controller 20 sets a scanning area of the controllable galvanometer scanner 11 to the partial area designated by the user, and sets the applied light sources of the laser unit 1 to both the laser light sources 2 and 3 (the ultraviolet laser light source and the argon laser light source).

At this time, the laser lights capable of being emitted from the laser unit 1 are both the argon laser light with 488 nm of wavelength and the ultraviolet laser light with 405 nm of wavelength.

Between them, the argon laser light can reach the sample 16 by passing through the light path R2 as shown by a solid line in FIG. 3, and a spot of the argon laser light can scan over the entire observation area of the sample 16 (refer to the lower part in FIG. 3) using the resonant galvanometer scanner 12. Since a fluorescence generated from the spot can be reflected by the dichroic mirror 9 as shown by a dotted line in FIG. 3, it is extracted to a side of the detecting optical system 100A.

Figure 4:
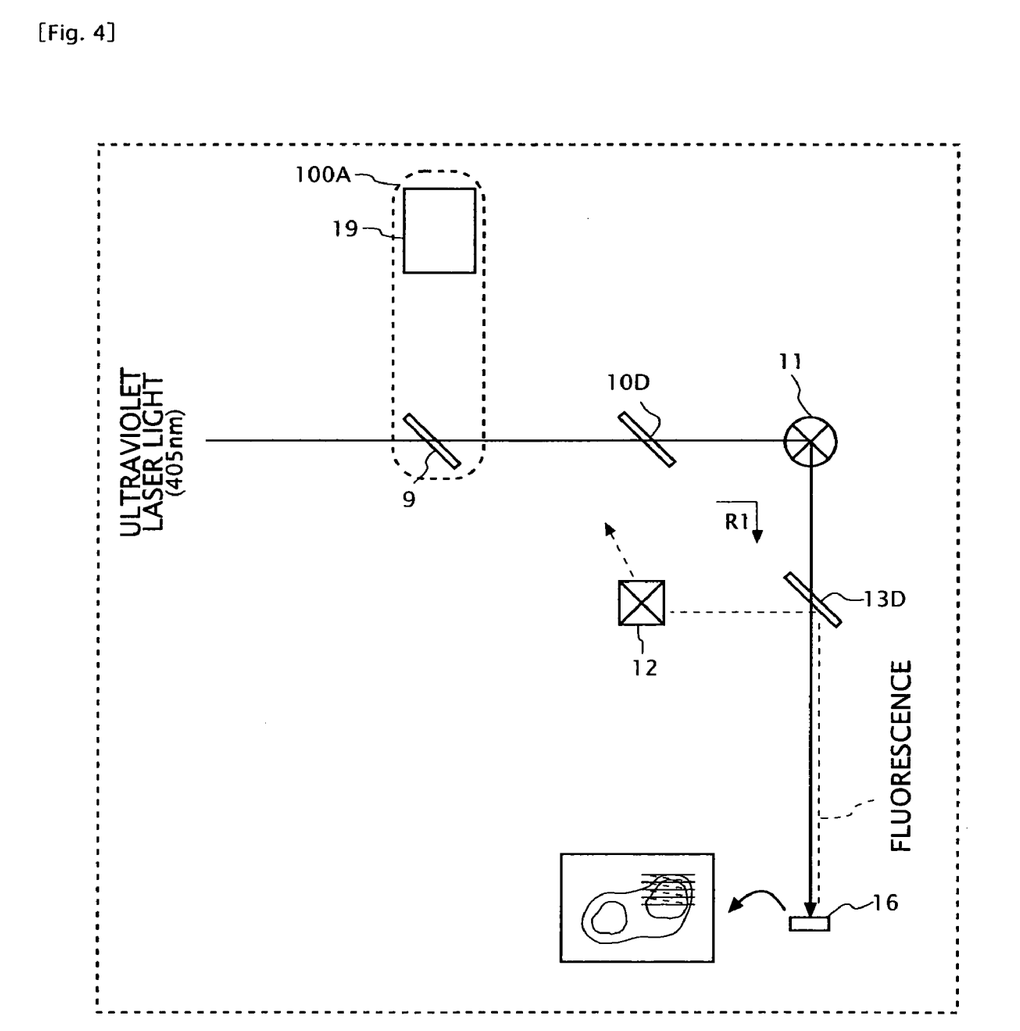
FIG. 4 is a conceptual diagram to explain a light path of ultraviolet laser light in the second embodiment.

Meanwhile, the ultraviolet laser light can reach the sample 16 by passing through the light path R1 as shown by a solid line in FIG. 4, and a spot of the ultraviolet laser light can scan over the partial area of the sample 16 (refer to a lower part in FIG. 4) using the controllable galvanometer scanner 11. Since a fluorescence generated from the spot (which is considered to be generated more or less) is reflected by the dichroic mirror 13D and incident on the resonant galvanometer scanner 12 as shown by a dotted line in FIG. 4, and thus it does not pass through the same scanner, no descan is occurred and the fluorescence does not pass through the pinhole of the detecting optical system 100A.

(Step 5)

The controller 20 applies the light stimulus to the partial area of the sample 16 (refer to the lower part in FIG. 4) with the ultraviolet laser light and performs an imaging of the entire observation area of the sample 16 (refer to the lower part in FIG. 3) with the argon laser light by driving the laser unit 1, the controllable galvanometer scanner 11, the resonant galvanometer scanner 12 and the light detector 19. Fluorescence image data of the sample 16 obtained through this imaging is transmitted to the computer 21.

(Step 6)

The computer 21 outputs the fluorescence image data of the sample 16 to the monitor 22. On the screen of the monitor 22, the user can observe the state of the sample 16 when the light stimulus is applied thereto. The computer 21 stores the fluorescence image data if necessary (the above description corresponds to the step 6).

As above, in the present embodiment, the system of the first embodiment, in which, particularly the dichroic mirrors 10D and 13D of the light path switching units 10 and 13 are effectively utilized, so that it is possible to simultaneously conduct the light stimulus and the imaging.

Further, in the aforementioned step 5, the light stimulus (the driving of the laser light source 2 and the controllable galvanometer scanner 11) and the imaging (the driving of the laser light source 3, the resonant galvanometer scanner 12 and the light detector 19) are respectively performed only once, but, the imaging can be continuously and repeatedly conducted. In that case, the fluorescence image data of successive plurality of frames can be obtained, which enables to observe a temporal change of the sample 16 right after the light stimulus is applied thereto.

Further, in the aforementioned step 1, the combination of set elements of the light path switching units 10 and 13 is set to that of dichroic mirrors 10D and 13D, but, it may be set to a combination of all-reflective mirrors 10M and 13M. However, in such a case, there is a need to change, in step 4, the combination of set elements of the light path switching units 10 and 13 to that of dichroic mirrors 10D and 13D.

Third Embodiment

Hereinafter, a third embodiment will be described. The present embodiment is an embodiment of a light stimulus observation method in which the system of the first embodiment is utilized and a light source used in common for the light stimulus and the imaging is applied.

Here, the excitation wavelength of the fluorescent dye applied to the sample 16 is set to 488 nm, and the wavelength of the light stimulus to be given to the sample 16 is set to 488 nm.

In this case, the main body of microscope 100 is set as follows, for instance.

Laser light source 2: argon laser light source (wavelength of 488 nm)

Dichroic mirror 9: dichroic mirror which transmits light of a short wavelength side including 488 nm and reflects light of a long wavelength side longer than 488 nm Note that in the present embodiment, the laser light source 2 and the dichroic mirrors 10D and 13D are not used, so that a setting thereof can be performed arbitrarily. Therefore, the setting of the main body of microscope 100 may be performed in the same manner as that of the main body of microscope 100 in the second embodiment.

Figure 5:
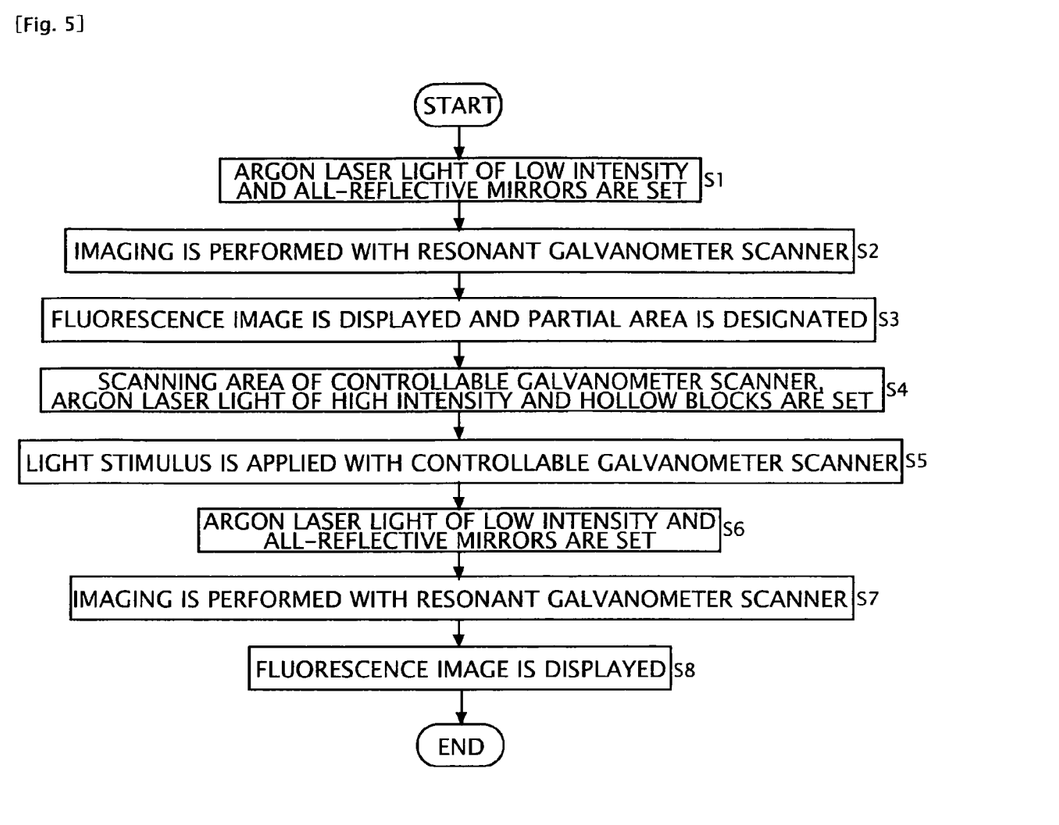
FIG. 5 is a view showing a procedure in a third embodiment.

A procedure of the light stimulus observation is as shown in FIG. 5.

(Step 1)

Figure 6:
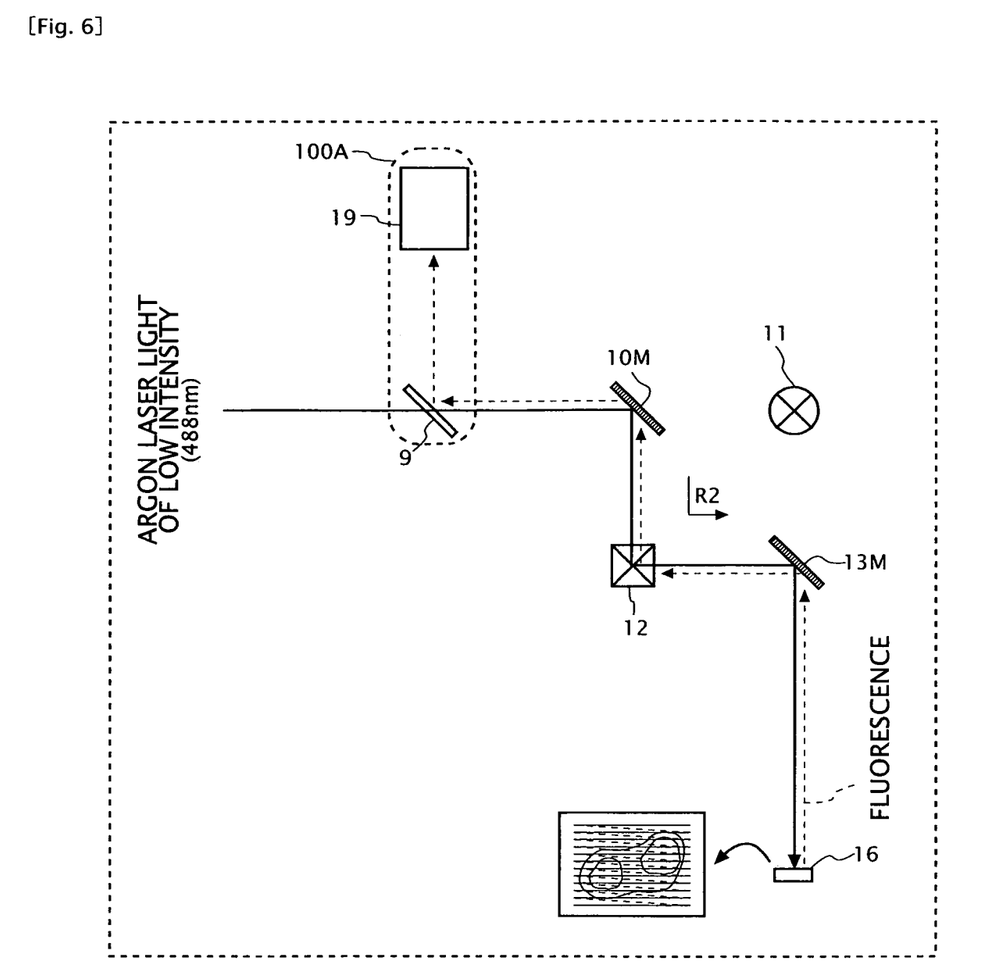
FIG. 6 is a conceptual diagram to explain a light path of argon laser light of low intensity in the third embodiment.

The controller 20 sets the applied light source of the laser unit 1 to the laser light source 3 (argon laser light source), and sets the combination of set elements of the light path switching units 10 and 13 to that of all-reflective mirrors 10M and 13M as shown in FIG. 6. Note that at this moment, an intensity of the emission light of the laser unit 1 is supposed to be set to an intensity for imaging (low intensity).

At this time, the laser light capable of being emitted from the laser unit 1 is only the argon laser light of low intensity. The argon laser light of low intensity can reach the sample 16 by passing through the light path R2 as shown by a solid line in FIG. 6, and a spot of the argon laser light can scan over the entire observation area of the sample 16 (refer to a lower part in FIG. 6) using the resonant galvanometer scanner 12. Since a fluorescence generated from the spot can be reflected by the dichroic mirror 9 as shown by a dotted line in FIG. 6, it is extracted to a side of the detecting optical system 100A.

(Step 2)

The controller 20 drives the laser unit 1, the resonant galvanometer scanner 12 and the light detector 19, and performs an imaging of the entire observation area of the sample 16 (refer to the lower part in FIG. 6) with the argon laser light of low intensity. Fluorescence image data of the sample 16 obtained through this imaging is transmitted to the computer 21.

(Step 3)

The computer 21 outputs the fluorescence image data of the sample 16 to the monitor 22 and gets a user to designate, on a screen of the monitor 22, a partial area to which the light stimulus is applied. Through the operation of the input device 23, the user designates a desired partial area with respect to the computer 21. Information regarding the partial area designated by the user is transmitted to the controller 20.

(Step 4)

Figure 7:
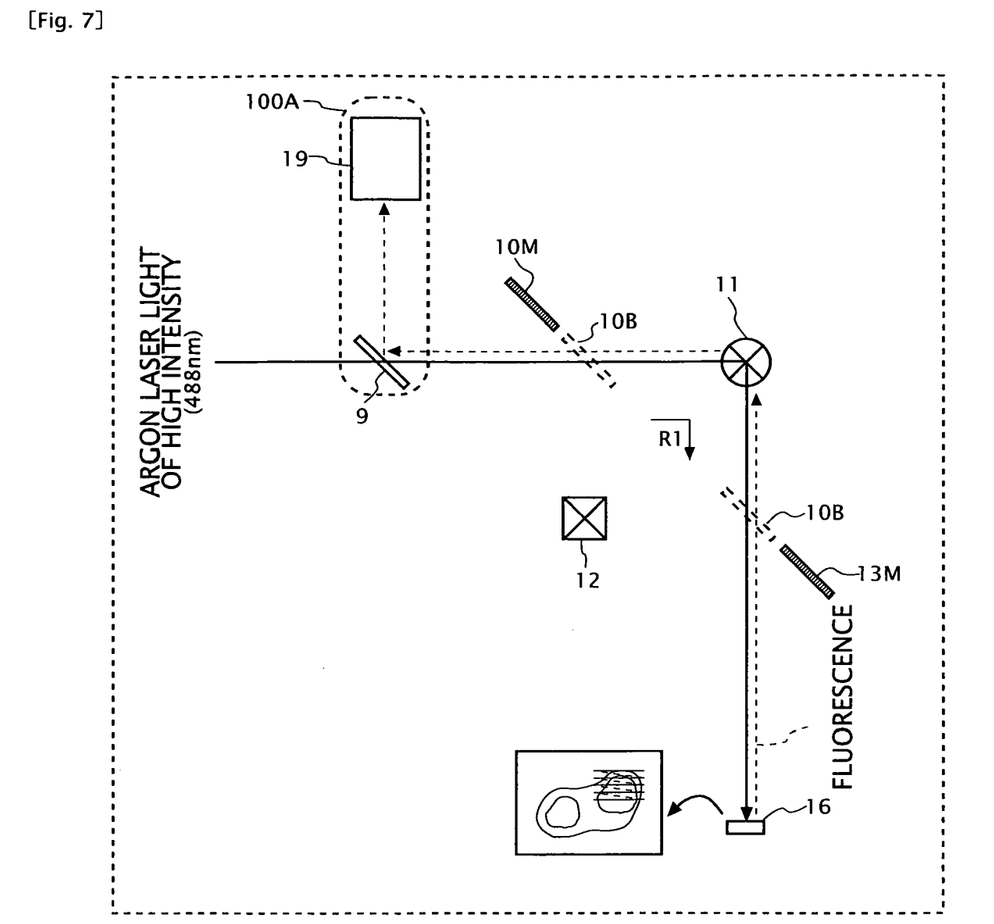
FIG. 7 is a conceptual diagram to explain a light path of argon laser light of high intensity in the third embodiment.

The controller 20 sets a scanning area of the controllable galvanometer scanner 11 to the partial area designated by the user. Further, the controller 20 changes the intensity of the emission light of the laser unit 1 to an intensity for light stimulus (high intensity), and changes the combination of set elements of the light path switching units 10 and 13 to that of hollow blocks 10B and 13B as shown in FIG. 7.

At this time, the laser light capable of being emitted from the laser unit 1 is only the argon laser light of high intensity. The argon laser light of high intensity can reach the sample 16 by passing through the light path R1 as shown by a solid line in FIG. 7, and a spot of the argon laser light can scan over the partial area of the sample 16 (refer to a lower part in FIG. 7) using the controllable galvanometer scanner 11. Since a fluorescence generated from the spot can be reflected by the dichroic mirror 9 as shown by a dotted line in FIG. 7, it is extracted to a side of the detecting optical system 100A.

(Step 5)

The controller 20 drives the laser unit 1 and the controllable galvanometer scanner 11, to thereby apply the light stimulus to the partial area of the sample 16 (refer to the lower part in FIG. 7) with the argon laser light of high intensity. Note that since it is not necessary to perform the imaging at this time, there is no need to drive the light detector 19.

(Step 6)

The controller 20 changes the intensity of the emission light of the laser unit 1 to the intensity for imaging (low intensity), and changes the combination of set elements of the light path switching units 10 and 13 to that of all-reflective mirrors 10M and 13M as shown in FIG. 6.

At this time, the laser light capable of being emitted from the laser unit 1 is only the argon laser light of low intensity.

The argon laser light of low intensity can reach the sample 16 by passing through the light path R2 as shown by a solid line in FIG. 6, and a spot of the argon laser light can scan over the entire observation area of the sample 16 (refer to the lower part in FIG. 6) using the resonant galvanometer scanner 12. Since a fluorescence generated from the spot can be reflected by the dichroic mirror 9 as shown by a dotted line in FIG. 6, it is extracted to a side of the detecting optical system 100A.

(Step 7)

The controller 20 drives the laser unit 1, the resonant galvanometer scanner 12 and the light detector 19 and performs an imaging of the entire observation area of the sample 16 (refer to the lower part in FIG. 6) with the argon laser light of low intensity. Fluorescence image data of the sample 16 obtained through this imaging is transmitted to the computer 21.

(Step 8)

The computer 21 outputs the fluorescence image data of the sample 16 to the monitor 22. On the screen of the monitor 22, the user can observe the state of the sample 16 right after the light stimulus is applied thereto. The computer 21 stores the fluorescence image data if necessary (the above description corresponds to the step 8).

As above, in the present embodiment, the system of the first embodiment, in which, particularly the hollow blocks 10B and 13B and the all-reflective mirrors 10M and 13M of the light path switching units 10 and 13 are effectively utilized, so that it is possible to apply the light source used in common for the light stimulus and the imaging.

Note that the imaging is performed only once in the aforementioned step 7, but, it can be continuously and repeatedly conducted. In that case, the fluorescence image data of successive plurality of frames can be obtained, which enables to observe a temporal change of the sample 16 right after the light stimulus is applied thereto.

[Other Features]

Note that in the aforementioned main body of microscope 100, the number of kinds of light sources to be mounted on the laser unit 1 is two, but, it may be three or more. Other than the ultraviolet laser light source and the argon laser light source, an IR laser light source (wavelength of 710 nm) used for a two-photon excitation or the like may be mounted.

Further, it is preferable to set the characteristics of the dichroic mirrors 9, 10D and 13D in accordance with the combination of light sources to be mounted. Incidentally, when the number of combinations of light sources is large, it is only required to prepare the dichroic mirrors with various characteristics and to use them properly. It is also allowable to previously equip the respective light path switching units 10 and 13 with a plurality of kinds of dichroic mirrors.

In the aforementioned main body of microscope 100, the optical elements to be mounted on the light path switching units 10 and 13 have three kinds, which are, the dichroic mirrors, the all-reflective mirrors and the hollow blocks, but, they may have two kinds of the all-reflective mirrors and the hollow blocks. Further, it is allowable to apply only the dichroic mirrors. Furthermore, it is also allowable to provide, instead of the dichroic mirrors (or in addition to the dichroic mirrors), beam splitters of another type such as half mirrors and inverse dichroic mirrors (ones with transmission wavelengths longer than reflection wavelengths). Note that an example of a light stimulus observation method using the half mirrors will be explained in a later-described fourth embodiment.

Incidentally, when the wavelength of the laser light used for the light stimulus is longer than that of the laser light used for the imaging, such as when the IR laser light source is used for the light stimulus, the use of inverse dichroic mirrors is effective.

Further, when the optical elements to be disposed on the branching points of the light paths R1 and R2 are the beam splitters and it is not necessary to switch the optical elements into another optical elements, the beam splitters may be left disposed without using the light path switching units 10 and 13.

Further, in the aforementioned main body of microscope 100, the mutually different kinds of galvanometer scanners (the controllable galvanometer scanner 11 and the resonant galvanometer scanner 12) are mounted as one pair of galvanometer scanners, but, the galvanometer scanners of the same kind may also be mounted. However, it is further preferable to mount the galvanometer scanners of different kinds since it becomes possible to use them separately (further, the members used are not limited to the galvanometer scanners and those capable of changing the direction of light such as, for instance, acoustic optical elements can also be applied).

Further, in the aforementioned main body of microscope 100, the separating number (changing number) of light path and the number of galvanometer scanners are respectively two, but the number may be increased to three or more so that the degree of freedom of observation is further enhanced.

Further, the aforementioned main body of microscope 100 is a laser scanning microscope having both the function of fluorescence detection and the function of confocal detection, but, the present invention is also applicable to a laser scanning microscope which does not have either or both of the function of fluorescence detection and the function of confocal detection.

Fourth Embodiment

Lastly, an example of the light stimulus observation method using the half mirrors will be briefly explained as a fourth embodiment. Here, description will be made on the assumption that the setting details of the main body of microscope 100 are the same as those of the main body of microscope 100 in the third embodiment.

Figure 8:
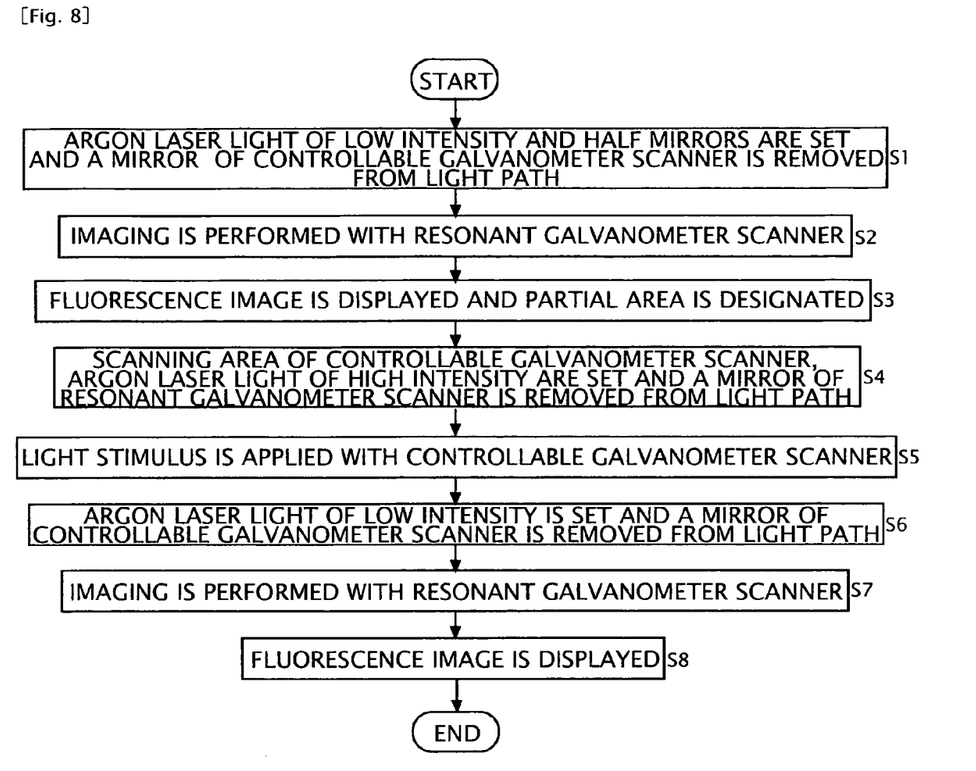
FIG. 8 is a view showing a procedure in a fourth embodiment.

A procedure of the light stimulus observation is as shown in FIG. 8.

(Step 1)

The controller 20 sets the applied light source of the laser unit 1 to the laser light source 3 (argon laser light source), and sets the set elements of the light path switching units 10 and 13 to the half mirrors. Note that at this moment, the intensity of the emission light of the laser unit 1 is supposed to be set to the intensity for imaging (low intensity).

Further, the controller 20 removes at least either of the galvanometer mirrors of the controllable galvanometer scanner 11 from the light path.

(Step 2)

The controller 20 drives the laser unit 1, the resonant galvanometer scanner 12 and the light detector 19, and performs an imaging of the entire observation area of the sample 16 with the argon laser light of low intensity. Fluorescence image data of the sample 16 obtained through the imaging is transmitted to the computer 21.

(Step 3)

The computer 21 outputs the fluorescence image data of the sample 16 to the monitor 22 and gets a user to designate, on the screen of the monitor 22, a partial area to which the light stimulus is applied. Through the operation of the input device 23, the user designates a desired partial area with respect to the computer 21. Information regarding the partial area designated by the user is transmitted to the controller 20.

(Step 4)

The controller 20 sets a scanning area of the controllable galvanometer scanner 11 to the partial area designated by the user. Further, the controller 20 changes the intensity of the emission light of the laser unit 1 to an intensity for light stimulus (high intensity).

Further, the controller 20 removes at least either of the galvanometer mirrors of the resonant galvanometer scanner 12 from the light path.

(Step 5)

The controller 20 drives the laser unit 1 and the controllable galvanometer scanner 11, to thereby apply the light stimulus to the partial area of the sample 16 with the argon laser light of high intensity. Note that there is no need to drive the light detector 19 at this time.

(Step 6)

The controller 20 changes the intensity of the laser light source 3 (argon laser light source) of the laser unit 1 to low intensity (for imaging).

Further, the controller 20 removes at least either of the galvanometer mirrors of the controllable galvanometer scanner 11 from the light path.

(Step 7)

The controller 20 drives the laser unit 1, the resonant galvanometer scanner 12 and the light detector 19 and performs an imaging of the entire observation area of the sample 16 with the argon laser light of low intensity. The obtained fluorescence image data of the sample 16 is transmitted to the computer 21.

(Step 8)

The computer 21 outputs the fluorescence image data of the sample 16 to the monitor 22. On the screen of the monitor 22, the user can observe the state of the sample 16 right after the light stimulus is applied thereto. The computer 21 stores the fluorescence image data if necessary (the above description corresponds to the step 8).

Note that the imaging is performed only once in the aforementioned step 7, but, it can be continuously and repeatedly conducted. In that case, the fluorescence image data of successive plurality of frames can be obtained, which enables to observe a temporal change of the sample 16 right after the light stimulus is applied thereto.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

What is claims is:

1. A laser scanning microscope, comprising:
    a light source;
        an optical unit guiding light from the light source to a specimen and guiding the light from the specimen to a detector;
        light path switching units switching a light path between the optical unit and the specimen to one among a plurality of light paths with different routes; and
        a plurality of light deflecting units each disposed in each of the plurality of light paths.

2. The laser scanning microscope according to claim 1, wherein
    the light path switching units include mirrors capable of being inserted into and/or removed from respective branching points of the plurality of light paths.

3. A laser scanning microscope, comprising:
    a light source;
    an optical unit guiding light from the light source to a specimen and guiding the light from the specimen to a detector;
    light path setting units separating a light path between the optical unit and the specimen into a plurality of light paths with different routes; and
    a plurality of light deflecting units each disposed in each of the plurality of light paths.

4. The laser scanning microscope according to claim 3, wherein
    the light path setting units include beam splitters disposed in respective branching points of the plurality of light paths.

5. The laser scanning microscope according to claim 1, wherein
    the light source, comprising
    a plurality of kinds of light sources with different wavelengths.

6. The laser scanning microscope according to claim 3, wherein
    the light source, comprising
    a plurality of kinds of light sources with different wavelengths.

7. The laser scanning microscope according to claim 1, wherein
    either one of the plurality of light deflecting units includes a resonant galvanometer scanner.

8. The laser scanning microscope according to claim 3, wherein
    either one of the plurality of light deflecting units includes a resonant galvanometer scanner.

9. An observation method utilizing a laser scanning microscope, the microscope comprising:
    a light source;
    an optical unit guiding light from the light source to a specimen and guiding the light from the specimen to a detector;
    a beam splitter separating a light path between the optical unit and the specimen into two light paths; and
    a first scanner disposed in one of the two light paths and a second scanner disposed in other one of the two light paths; wherein
    the observing method includes the steps of
    removing at least one of plurality of mirrors configuring the first scanner from the light path and obtaining a fluorescence image being generated by irradiating the light from the light source to the specimen through the second scanner, and
    removing at least one of plurality of mirrors configuring the second scanner from the light path and performing a light stimulus by irradiating the light from the light source to the specimen through the first scanner.

* * * * *